(12) United States Patent
Zhang et al.

(10) Patent No.: US 9,127,075 B2
(45) Date of Patent: Sep. 8, 2015

(54) ANALGESIC ACTIVE PEPTIDE VGG, PREPARATION AND USE THEREOF

(75) Inventors: Jianhai Zhang, Shenyang (CN); Zhou Yang, Shenyang (CN); Yanfeng Liu, Shenyang (CN); Chunfu Wu, Shenyang (CN)

(73) Assignee: SHENYANG PHARMACEUTICAL UNIVERSITY, Shenyang (CN)

( * ) Notice: Subject to any disclaimer, the term of this patent is extended or adjusted under 35 U.S.C. 154(b) by 20 days.

(21) Appl. No.: 13/825,249

(22) PCT Filed: Jul. 5, 2011

(86) PCT No.: PCT/CN2011/001103
§ 371 (c)(1),
(2), (4) Date: Mar. 20, 2013

(87) PCT Pub. No.: WO2012/003771
PCT Pub. Date: Mar. 29, 2012

(65) Prior Publication Data
US 2013/0225500 A1    Aug. 29, 2013

(30) Foreign Application Priority Data
Sep. 26, 2010 (CN) .......................... 2010 1 0291461

(51) Int. Cl.
*A61K 38/00* (2006.01)
*A61K 35/646* (2015.01)
*C07K 14/435* (2006.01)

(52) U.S. Cl.
CPC ......... *C07K 14/43522* (2013.01); *A61K 35/646* (2013.01); *A61K 38/00* (2013.01)

(58) Field of Classification Search
None
See application file for complete search history.

(56) References Cited

PUBLICATIONS

Zhu et al., Biochem. & Biophys. Res. Comm., 2010, 391, pp. 627-633.*
Ye et al., Toxicon, 2001, 39, pp. 1191-1194.*
Zhu et al., Biochem & Biophys. Res. Comm., 2010, 391, 627-633.*
Ye et al., Toxicon, 2001, 39, 1191-1194.*
Wu et al., Pure Appl. Chem., 1999, 71(6), 1157-1162.*

* cited by examiner

*Primary Examiner* — Karlheinz R Skowronek
*Assistant Examiner* — Roy Teller
(74) *Attorney, Agent, or Firm* — CBM Patent Consulting, LLC

(57) ABSTRACT

The present invention provides an active peptide purified from scorpions, and derivatives, analogs and active fragment which are produced by using genetic engineering technology. The analgesic active peptide VGG is extracted, separated and purified from scorpion, and its amino acid sequence is shown as below:

VKDGYIADDRNCPYFCGRNAYCDGECKKNRAESGYCQWASKYGNACWCY
KLPDDARIMKPGRCNGG.

The present invention further provides a use of the peptides in preparation of an analgesic drug, where the peptide is mixed with a pharmaceutically acceptable carrier to prepare into forms for injection, oral administration, transdermal absorption, and transmucosal absorption.

1 Claim, No Drawings

SEQUENCE LISTING

```
<160> NUMBER OF SEQ ID NOS: 9

<210> SEQ ID NO 1
<211> LENGTH: 198
<212> TYPE: DNA
<213> ORGANISM: Mesobuthus martensi

<400> SEQUENCE: 1
gtaaaggatg gttatattgc tgacgataga aactgcccat acttttgtgg tagaaatgca      60
tattgcgatg gagaatgtaa gaagaaccgt gctgagagtg gctattgcca atgggcaagt     120
aaatacggaa acgcctgctg gtgctataag ttgcccgatg atgcacgtat tatgaaacca     180
ggaagatgca atggcggt                                                   198

<210> SEQ ID NO 2
<211> LENGTH: 66
<212> TYPE: PRT
<213> ORGANISM: Mesobuthus martensi
```

<400> SEQUENCE: 2

Val Lys Asp Gly Tyr Ile Ala Asp Asp Arg Asn Cys Pro Tyr Phe Cys
1               5                   10                  15

Gly Arg Asn Ala Tyr Cys Asp Gly Glu Cys Lys Lys Asn Arg Ala Glu
                20                  25                  30

Ser Gly Tyr Cys Gln Trp Ala Ser Lys Tyr Gly Asn Ala Cys Trp Cys
            35                  40                  45

Tyr Lys Leu Pro Asp Asp Ala Arg Ile Met Lys Pro Gly Arg Cys Asn
        50                  55                  60

Gly Gly
65

<210> SEQ ID NO 3
<211> LENGTH: 83
<212> TYPE: PRT
<213> ORGANISM: Artificial Sequence
<220> FEATURE:
<223> OTHER INFORMATION: The sequence is synthesized

<400> SEQUENCE: 3

Met His His His His His Ser Gly Gly Gly Ser Gly Gly
1               5                   10                  15

Gly Val Lys Asp Gly Tyr Ile Ala Asp Asp Arg Asn Cys Pro Tyr Phe
                20                  25                  30

Cys Gly Arg Asn Ala Tyr Cys Asp Gly Glu Cys Lys Lys Asn Arg Ala
            35                  40                  45

Glu Ser Gly Tyr Cys Gln Trp Ala Ser Lys Tyr Gly Asn Ala Cys Trp
        50                  55                  60

Cys Tyr Lys Leu Pro Asp Asp Ala Arg Ile Met Lys Pro Gly Arg Cys
65                  70                  75                  80

Asn Gly Gly

<210> SEQ ID NO 4
<211> LENGTH: 67
<212> TYPE: PRT
<213> ORGANISM: Artificial Sequence
<220> FEATURE:
<223> OTHER INFORMATION: The sequence is synthesized.

<400> SEQUENCE: 4

Met Val Lys Asp Gly Tyr Ile Ala Asp Asp Arg Asn Cys Pro Tyr Phe
1               5                   10                  15

Cys Gly Arg Asn Ala Tyr Cys Asp Gly Glu Cys Lys Lys Asn Arg Ala
                20                  25                  30

Glu Ser Gly Tyr Cys Gln Trp Ala Ser Lys Tyr Gly Asn Ala Cys Trp
            35                  40                  45

Cys Tyr Lys Leu Pro Asp Asp Ala Arg Ile Met Lys Pro Gly Arg Cys
        50                  55                  60

Asn Gly Gly
65

<210> SEQ ID NO 5
<211> LENGTH: 17
<212> TYPE: PRT
<213> ORGANISM: Artificial Sequence
<220> FEATURE:
<223> OTHER INFORMATION: The sequence is synthesized.

<400> SEQUENCE: 5

```
Met His His His His His His Ser Gly Gly Gly Gly Ser Gly Gly Gly
1               5                   10                  15

Gly

<210> SEQ ID NO 6
<211> LENGTH: 63
<212> TYPE: DNA
<213> ORGANISM: Artificial Sequence
<220> FEATURE:
<223> OTHER INFORMATION: The sequence is synthesized.

<400> SEQUENCE: 6
catcatcatc atcatcacag cggcggcggc ggcagcggcg gcggcggcgt aaaggatggt    60
tat                                                                 63

<210> SEQ ID NO 7
<211> LENGTH: 18
<212> TYPE: DNA
<213> ORGANISM: Artificial Sequence
<220> FEATURE:
<223> OTHER INFORMATION: The sequence is synthesized.

<400> SEQUENCE: 7
ccgccattgc atcttcct                                                 18

<210> SEQ ID NO 8
<211> LENGTH: 21
<212> TYPE: DNA
<213> ORGANISM: Artificial Sequence
<220> FEATURE:
<223> OTHER INFORMATION: The sequence is synthesized.

<400> SEQUENCE: 8
gatatcgtaa aggatggtta t                                             21

<210> SEQ ID NO 9
<211> LENGTH: 29
<212> TYPE: DNA
<213> ORGANISM: Artificial Sequence
<220> FEATURE:
<223> OTHER INFORMATION: The sequence is synthesized.

<400> SEQUENCE: 9
ggaattctta accgccattg catcttcct                                     29
```

ANALGESIC ACTIVE PEPTIDE VGG, PREPARATION AND USE THEREOF

TECHNICAL FIELD

The present invention is related to the field of biomedical technology, involving the structure, preparation, biological activity and application of analgesic active peptide VGG. Specifically, this invention relates to the structure and preparation of an analgesic peptide VGG, the derivatives, analogues and active fragments of it. Analgesic active peptide VGG is commonly used as an analgesic agent in the medical field.

TECHNICAL BACKGROUND

As previous medical reports in Chinese medicine, scorpion is known as "Quanchong" or "Quanxie". The earliest record can be traced back to the *Kaibao's Herbal Classic* and listed in volume 40, the worm section of *Compendium of Materia Medica*, which has been over 2000 years medical history. The scorpion has been proved to have effects for extinguishing endogenous wind and suppressing pain, relieving internal fever and dissipating stagnation, activating meridian and alleviating pain. It is clinically used to treat migraine, peripheral facial paralysis, rheumatism pain and cancer pain, etc., which are proved to be effective. The active ingredient of the scorpion is the toxin secreted by the caudal gland. The toxin contains a lot of active components with high pharmaceutical values, and it is a natural active peptide pool that contains various multi-functional peptides.

However, only few of analgesic active ingredients have been separated, purified and structure analyzed from the scorpion or scorpion venom, such as the analgesic-antitumor peptide and analgesic-antimicrobial active peptide, etc.

DETAILED DESCRIPTION OF INVENTION

The purpose of the present invention was to provide analgesic active peptide VGG and its applications. Specifically, it was to obtain the analgesic active peptide VGG from scorpion venom, scorpion tail and/or scorpion body through screening, separation and purification. And the protein extraction, separation and purification techniques were used. The process for preparing analgesic active peptide VGG is simple and practicable, and the analgesic active peptide VGG can be mixed with pharmaceutically acceptable composition to make therapeutic medicines.

In the present invention, a novel polypeptide was obtained from scorpion body or scorpion tail or scorpion venom by screening, separation and purification. Meanwhile, the polypeptide was also prepared by genetic engineering technology or chemical synthesis technology. Furthermore, the instant invention produced the analgesic derivates, analogues, active fragments of the analgesic active peptide by using the genetic engineering technology or chemical synthesis technology.

The analgesic active peptide VGG, which has the amino acid sequence as showed in SEQ ID NO: 2, was extracted, separated and purified from scorpion venom or scorpion tails or scorpion body.

The analgesic active peptide VGG was obtained by following procedures, which includes: (1) raw material (scorpion venom or scorpion tail or scorpion body) was homogenated, dissolved in distilled water or acid solution or alkaline solution, the insoluble impurities were removed from homogenate by centrifuge, the upper solution was taken as the leaching liquid; (2) the crude analgesic active peptide VGG was obtained by applying the leaching liquid on different combination of hydrophobic chromatography, ion exchange chromatography, and gel filtration chromatography and ultrafiltration to remove salt, non-essential proteins and concentration; (3) the highly pure analgesic active peptide VGG was obtained by using reversed phase chromatographic column. For example, the scorpion venom was dissolved in the acid solution and the insoluble impurities was removed by centrifuge and the leaching liquid is yielded; the hydrophobic chromatography separation was used to get the analgesic active component I from the leaching liquid; the salt and non-essential proteins were removed by ultrafiltration from the analgesic active component I, then the analgesic active component II was yielded by running through ion exchange chromatographic column separation after concentration; the analgesic active component III was yielded through the further separation of hydrophobic chromatography; the analgesic active component IV was yielded by running through ion exchange and chromatographic column purification after the salts in analgesic active component III was removed by ultrafiltration and was concentrated; the analgesic active peptide VGG was further purified by a gel filtration chromatography; then the purest analgesic active peptide VGG was yielded by a reversed phase chromatographic column.

The second purpose of this invention was to provide preparation methods of multiple types of analgesic active peptide VGG and its derivatives, analogues and active fragments, including producing them through genetic engineering technology or obtain them by chemical synthesis. The process disclosed in this invention is conventional, simple and upscale production. It is not only of important guidance significance and practical value but also provides important information for the related pharmaceutical industry.

Another purpose of this invention was to provide the preparation methods of analgesic active peptide VGG and its derivatives, analogues and active fragments that were produced by the genetic engineering method, including:

(1) The nucleic acids encoding the analgesic active peptide VGG and its derivatives, analogues and active fragments were cloned into expression vectors;

(2) The above expression vectors were introduced into the proper host cells (either prokaryotic cell or eukaryotic cell);

(3) At the suitable expressing condition, the hosts containing the expression vectors were cultured;

(4) The host and culture media were collected, and the desired proteins were collected.

This invention provides the separation and purification methods of expression products of the analgesic active peptide VGG and its derivatives, analogues and active fragments. The purification process included salting-out and precipitation, ultrafiltration, affinity chromatography, icon-exchange chromatography, hydrophobic chromatography and gel filtration chromatography, etc. The expressing production can be presented in lysates of hosts or/and culture media. The SDS-PAGE, ELISA or WESTERN blot analysis were used to detect/monitor the desired products.

In the present invention, the in vivo experiment for analgesic biologic activity was carried out in mouse with the analgesic active peptide VGG and its derivatives, analogues and active fragments.

This invention also provides the application of the analgesic active peptide VGG and its derivatives, analogues and active fragments in the biopharmaceutical field. Specifically, it includes the analgesic biologic activity.

Another purpose of this invention was to provide one kind or multiple kinds of acceptable carriers or drug combinations of excipient that contain the above limited protein. According to the basic principle and method of the pharmaceutical industrial field to prepare non-oral administration route drug combination (see also *Remington's Pharmaceutical Science*, 15th, Mack Publishing Company, 1980). Patients may use the drug combinations of this medicine through various administration routes, especially, through vein, muscle, joint, abdominal cavity, nose, intracutaneous organization and subcutaneous organization, etc.

Another purpose of this invention was to provide the application of the above limited protein in the production of analgesic drugs. Protein or drug combinations that contain the protein in this invention may be used as therapeutic agent to treat specific types of pains and relevant diseases. Effective dosage of the drug combination of this invention subjected to various factors of the nature, severity and sensitive adaptability of the disease and administration route. Therefore the dosage shall be determined by the clinical doctor on the individualized principle.

In this invention, the term "host cell" includes the prokaryotic cell or eukaryotic cell, the frequently-used example of prokaryotic cell includes the *Escherichia coli*, *Bacillus subtilis*, etc. And the frequently-used example of the eukaryotic cell includes the yeast cell, insect cell and mammalian cell, etc.

EXAMPLES

The following examples make the person skilled in the art understand the invention comprehensively instead of limit the scope of the notarized right in any way.

Example 1

To Produce Analgesic Active Peptide VGG from the Scorpion Venom

The basic conditions of the extraction, separation and purification system for producing the analgesic active peptide VGG: the temperature was maintained between 0° C. and 45° C.; pH value of the solution was between pH2 and pH12, the optimum pH value scope was between pH5 and pH9. The above conditions will not damage the physicochemical property of the adopted media of extraction, separation and purification, nor affect the activity of the analgesic active peptide VGG.

(1) Leaching of the Analgesic Active Ingredient

Leach the Analgesic Active Ingredient though the following three methods:

A. The scorpion venom was dissolved in the distilled water which was centrifuged at 15000 rpm for 15 minutes. The pH of supernatant was adjusted to 2 with 0.01M hydrochloric acid or phosphoric solution, centrifuged at 15000 rpm for 15 minutes. Then, the pH of supernatant was adjusted to 12, centrifuged at 15000 rpm for 15 minutes. The final supernatant was named as leaching liquid containing scorpion venom analgesic active ingredient.

B. The scorpion venom was dissolved in the buffer solution or acid solution with a pH value of 2, centrifuged at 15000 rpm for 15 minutes. The pH of supernatant was adjusted to 12 with alkaline solution, centrifuged at 15000 rpm for 15 minutes. The supernatant was leaching liquid containing scorpion venom analgesic active ingredient.

C. The scorpion venom was dissolved in the buffer solution or alkaline solution with a pH value of 12, centrifuged at 15000 rpm for 15 minutes. The pH of supernatant was adjusted to 2 with acid solution, centrifuged at 15000 rpm for 15 minutes. The resultant supernatant was leaching liquid containing scorpion venom analgesic active ingredient.

The above leaching liquid with pH2-pH12 had the active ingredient from the material without affecting the biological activity of the analgesic active peptide VGG.

(2) Hydrophobic Chromatographic Column Separation for Analgesic Active Peptide VGG The pH of leaching liquid, which contains with analgesic active ingredients, was adjust to between 5 and 9 with hydrochloric acid solution or phosphoric acid solution or acid solution or alkaline solution; the neutral salt was added upto the concentration reaches 2M, which was loaded in the hydrophobic chromatographic column pre-balanced with 2M neutral salt buffer, and then eluted with neutral salt buffer solution of 2.0 M, 1.5 M, 1.0 M, 0.5 M, and finally eluted with the buffer solution which was mixed with the analgesic active elution buffer. The mixture was the analgesic active ingredient I.

Features of the Hydrophobic Chromatographic Column Separation: 1. the phenyl-hydrophobic chromatography packing or the octyl-hydrophobic chromatography packing or the hexyl-hydrophobic chromatography packing or the butyl-hydrophobic chromatography packing were used; 2. the neutral salt was selected among the $(NH_4)_2SO_4$ or $Na_2SO_4$ or NaCl; 3. The buffer solution with pH2-pH12 do not affect the biological activity of the analgesic active ingredient and the separation of the ingredient, the optimum pH value was between pH5 and pH9; 4. The concentration of buffer solution was between 1 mM and 100 mM, the optimum concentration was between 10 mM and 50 mM, under which neither the biological activity of the analgesic active ingredient nor the separation of the ingredient is affected.

(3) Ultrafiltration of the Analgesic Active Ingredient Solution

The ultrafiltration is used to remove salt and non-essential proteins of the analgesic active ingredient solution or to replace the buffer solution, and also to concentrate the analgesic active ingredient solution. The selected ultrafiltration membrane allowed the analgesic active peptide VGG to permeate. The solution, which excluded non-essential proteins and contained the analgesic active peptide VGG, was collected after the ultrafiltration. A different ultrafiltration membrane, which was able retain the analgesic active peptide VGG, was selected to concentrate the analgesic active peptide VGG.

Features of the ultrafiltration: 1. permeation of analgesic active peptide VGG was selected from the ultrafiltration membrane of 10 kDa, 20 kDa, 30 kDa, 40 kDa or 50 kDa, the optimum ultrafiltration membrane is 30 kDa, ultrafiltration membrane that was bigger or smaller than 30 kDa affected the yield or/and ultrafiltration efficiency; 2. retention of analgesic active peptide VGG was selected from the ultrafiltration membrane of 1 kDa, 2 kDa, 3 kDa or 5 kDa, the optimum membrane is 1 kDa, the ultrafiltration membrane that is bigger or smaller than 1 kDa affected the yield or/and ultrafiltration efficiency; 3. ultrafiltration temperature was between 0° C. and 45° C., which did not damage the physicochemical property of the ultrafiltration membrane and the activity of the analgesic active peptide VGG (4) Ion-exchange and Chromatographic Column Separation of the Analgesic Active Peptide VGG This step is used to remove salt, to replace buffer solution and to concentrate the analgesic active ingredient I solution which was yielded in Method (3) through ultrafiltration. The sample solution was loaded to the prepared icon-exchange chromatographic column that has been balanced by the buffer solution. First remove the non-absorptive non-essential proteins by fully washing with the buffer solution, then the salt solution of 0.05M, 0.1M, 0.15M, 0.2M, 0.25M, 0.3M, 0.4M, and 0.5M were used for staged elution; the eluents that contain analgesic active ingredients were named as the analgesic active ingredient II.

Features of the Ion-exchange and Chromatographic Column Separation: 1. the chromatographic medium was selected from cation exchange chromatography packing, such as CM-icon-exchange chromatography packing or SP-icon-exchange chromatography packing or the S-ion-exchange chromatography packing, etc. The pH value of the buffer solution was selected between pH2 and pH7, and the optimum pH value was between pH5 and pH7; 2. The chromatographic medium was selected from the anion exchange chromatography packing, such as the Q-ion-exchange chromatography packing or the DEAE-ion-exchange chromatography packing or the QAE-ion-exchange chromatography packing. The pH of buffer solution was selected 7 and 12, and the optimum pH value was between pH7 and pH9; 3. The concentration of the buffer solution was selected between 1 mM and 50 mM, and the optimum concentration was between 10 mM and 25 mM. The condition stated above did not affect the biological activity of the analgesic active ingredient and the separation of active ingredient; 4. saline solution of the staged elution was the buffer solution with a specific concentration, or some neutral salt was added to the buffer solution with the optimum concentration till reaches the concentration that we desired; 5. the neutral salt was selected from $(NH_4)_2SO_4$ or $Na_2SO_4$ or NaCl or KCl, and the NaCl was the best choice.

(5) Further Hydrophobic Chromatographic Column Separation of Analgesic Active Peptide VGG Further purifying the analgesic active ingredient II obtained with above method (2): The neutral saline was added to the analgesic active ingredient solution till the concentration reaches 2M, which was loaded to the hydrophobic chromatographic column pre-balanced with 2M neutral salt buffer, and then the gradient elution was conducted with neutral salt buffer solution (2.0 M and 0.0 M), the eluent peaks which contain analgesic active ingredient were collected and mixed as the analgesic active ingredient III, and finally the salts were removed through ultrafiltration and then as the analgesic active ingredient III was concentrated.

Features of the Hydrophobic Chromatographic Column Separation: 1. the Hydrophobic Chromatographic medium was selected from the phenyl-hydrophobic chromatography packing or the octyl-hydrophobic chromatography packing or the hexyl-hydrophobic chromatography packing or the butyl-hydrophobic chromatography packing; 2. the neutral salt was selected from the $(NH_4)_2SO_4$ or $Na_2SO_4$ or NaCl; 3. The pH value of buffer solution is between pH2 and pH12, and the optimum pH value is between pH5 and pH9; 4. The concentration of buffer solution is between 1 mM and 100 mM, and the optimum concentration is between 10 mM and 50 mM.

(6) Ion-Exchange and Further Chromatographic Column Separation of the Analgesic Active Peptide VGG Further purifying the analgesic active ingredient III obtained with the above method (4). The sample was loaded to the prepared icon-exchange chromatographic column that was balanced by buffer solution, the non-absorptive non-essential proteins were washed out, and then the gradient elution was conducted with neutral salt buffer solution between (0.0 M and 1.0 M), the eluent peaks which contain analgesic active ingredients were collected and mixed as the analgesic active ingredient IV.

Features of the Ion-exchange and Chromatographic Column Separation: 1. the chromatographic medium was selected from the cation exchange chromatography packing, such as CM-ion-exchange chromatography packing or SP-ion-exchange chromatography packing or the S-ion-exchange chromatography packing, etc. The pH value of the buffer solution is selected between pH2 and pH7, and the optimum pH value was between pH5 and pH7; 2. The chromatographic medium was selected from the anion exchange chromatography packing, such as the Q-ion-exchange chromatography packing or the DEAE-ion-exchange chromatography packing or the QAE-ion-exchange chromatography packing. The pH of buffer solution is selected between pH7 and pH12, and the optimum pH value was between pH7 and pH9; 3. the concentration of the buffer solution was selected between 1 mM and 50 mM, and the optimum concentration was between 10 mM and 25 mM; 4. saline solution of the staged elution was the buffer solution with a specific concentration, or some neutral salt was added to the buffer solution with the optimum concentration till reaches the concentration that we desired; 5. the neutral salt was selected from $(NH_4)_2SO_4$ or $Na_2SO_4$ or NaCl or KCl, and the NaCl was the best choice.

(7) Gel Filtration Chromatographic Column Purification of the Analgesic Active Peptide VGG To ultrafiltrate and concentrate the solution that contains analgesic active ingredient IV: the sample solution was loaded to the gel filtration chromatographic column which was balanced by eluent, then the eluent peak that contains analgesic active ingredient was collected as Analgesic Active Peptide VGG.

Features of the Gel Filtration and Chromatographic Column Seperation: 1. the chromatography media was selected from Gel chromatography packing, such as Sephacryl S-100 HR or Sephacryl S-200 HR or Sephadex G-50 or Sephadex G-75 or Sephadex G-100 or Sephadex G-150 or Superose 12 prep grade or Superose 6 prep grade or Superdex 30 prep grade or Superdex 75 prep grade or Superose 12 HR or Superose 6 HR or Superdex Peptide HR or Superdex75 HR or Superdex Peptide PE; 2. pH value of the eluent was between pH2-pH12, and the optimum pH value was between pH5-pH9; 3. the ion concentration of the eluent was 0.15M or above.

(8) Reversed Phase Chromatographic High Purity Purification of the Analgesic Active Peptide VGG The analgesic active peptide VGG obtained in method (7) was loaded to the reversed phase chromatographic column that was balanced by the eluent, the biggest eluent peak, one of the eluent peaks, that contain analgesic active ingredient was collected.

Features of the Reversed Phase and Chromatographic Separation: 1. the SOURCE 15RPC or 30RPC was the chromatography packing for the reversed phase; 2. the organic solvents of the eluent was selected from acetonitrile, methanol, and tetrahydrofuran; 3. the pH value of the eluent was between pH2 and pH12, and the optimum pH value was between pH2 and pH8; 4. the concentration of organic solvents of the eluent was 20%-95%; 5. the elution mode was gradient mode or staged mode. The analgesic active peptide VGG obtained from the scorpion venom has an amino acid sequence as showed in SEQ ID NO: 2.

Example 2

Analgesic Active Peptide VGG is Obtained from the Scorpion Tails

The tactics, basic approach and the basic process of this example is the same as example 1.

(1) Extraction of the Analgesic Active Ingredients

A. The scorpion tails were dissolved in the distilled water, and the homogenate was centrifuged at 15000 rpm for 15 min; the pH of supernatant was adjusted to 2 with 0.01M of hydrochloric acid or phosphoric acid solution or acid solution, then centrifuged at 15000 rpm for 15 min; the pH of resultant supernatant was adjusted to 12 with alkaline solution, then centrifuged at 15000 rpm for 15 min; the final supernatant was named as the extraction of analgesic active ingredients of scorpion tails.

B. The scorpion tails were homogenized with buffer solution or acid solution of pH value of 2, centrifuged at 15000 rpm for 15 min; the pH of supernatant was adjusted to 12 with alkaline solution, then centrifuged at 15000 rpm for 15 min; the final supernatant was named the extraction of analgesic active ingredients of scorpion tails.

C. The scorpion tails were homogenized with buffer solution or acid solution of pH value of 12, centrifuged at 15000 rpm for 15 min; the pH of supernatant was adjusted to 2 with acid solution, and centrifuged at 15000 rpm for 15 min; the final supernatant is the extraction of analgesic active ingredients of scorpion tails.

The pH values of the above extractions were 2-12, which did not affect the bioactivity of the analgesic active ingredients, and the active ingredients can be extracted from the raw material.

(2) Separation and Purification and High-Purity Purification of the Analgesic Active Peptide VGG The extraction of the above analgesic active ingredients is the same as the tactic, basic approach and the basic process separation and purification of the analgesic active peptide VGG stated in (2)-(8) of example 1.

The analgesic active peptide VGG obtained from the scorpion tail has an amino acid sequence as showed in SEQ ID NO: 2.

Example 3

Analgesic Active Peptide VGG was Extracted from the Scorpion Body

The tactic, basic approach and the basic process of this example was the same as example 2.

(1) Extraction of the Analgesic Active Ingredients

A. The scorpion body was dissolved in the distilled water, and the homogenate was centrifuged at 15000 rpm for 15 min; the pH of supernatant was adjusted to 2 with 0.01M of hydrochloric acid or phosphoric acid solution or acid solution, then centrifuged at 15000 rpm for 15 min; the pH of resultant supernatant was adjusted to 12 with alkaline solution, then centrifuged at 15000 rpm for 15 min; the final supernatant was named as the extraction of analgesic active ingredients of scorpion body.

B. The scorpion body was homogenized with buffer solution or acid solution of pH value of 2, centrifuged at 15000 rpm for 15 min; the pH of supernatant was adjusted to 12 with alkaline solution, then centrifuged at 15000 rpm for 15 min; the final supernatant was named the extraction of analgesic active ingredients of scorpion body.

C. The scorpion body was homogenized with buffer solution or acid solution of pH value of 12, centrifuged at 15000 rpm for 15 min; the pH of supernatant was adjusted to 2 with acid solution, and centrifuged at 15000 rpm for 15 min; the final supernatant is the extraction of analgesic active ingredients of scorpion body.

The pH values of the above extractions were 2-12, which did not affect the bioactivity of the analgesic active ingredients, and the active ingredients can be extracted from the raw material.

The extraction of the above analgesic active ingredients is the same as the tactic, basic approach and the basic process separation and purification of the analgesic active peptide VGG stated in (2)-(8) of example 1.

The analgesic active peptide VGG obtained from the scorpion tail has an amino acid sequence as showed in SEQ ID NO: 2.

Example 4

Extraction of the Analgesic Active Peptide VGG

The tactics and basic approach and the basic process of this example were the same as example 1.

The tactics, basic approach and the basic process of analgesic active ingredients extraction of the scorpion venom or scorpion tails or scorpion body was the same as the example 1, 2 and 3.

The tactics, basic approach and the basic process of analgesic active peptide VGG separation and separation was the same as example 1. The Analgesic active peptide VGG extraction was obtained by removing salt, non-essential proteins, and the concentrated analgesic active peptide VGG was obtained through various combination of hydrophobic chromatographic column, ion-exchange chromatographic column and gel filtration chromatographic column and ultrafiltration and the high-purified analgesic active peptide VGG was run on a reversed phase chromatographic column.

Characteristics of above combination: the analgesic active ingredients were isolated by running 1, through—ion-exchange chromatographic separation-hydrophobic chromatographic separation,—ion-exchange chromatographic further separation-hydrophobic chromatographic further separation-gel chromatographic purification-reversed phase chromatographic; 2, through gel chromatographic purification-ion-exchange chromatographic separation-hydrophobic chromatographic separation-ion-exchange chromatographic further separation-hydrophobic chromatographic further separation-reversed phase chromatographic; 3, through gel chromatographic purification-hydrophobic chromatographic separation-ion-exchange chromatographic separation-hydrophobic chromatographic separation-ion-exchange chromatographic separation-reversed phase chromatographic; 4, the sequence of above separation and purification can be random, which can produce pure the analgesic active peptide VGG The analgesic active peptide VGG has an amino acid sequence as showed in SEQ ID NO: 2.

Example 5

To produce the Analgesic Active Peptide VGG and its Derivative, Analogue and Active Fragment 1. the Recombinant Analgesic Active Peptide VGG Gene Construction This example is used to describe the basic techniques and strategy for constructing an expression gene which expresses the analgesic active peptide VGG of instant invention and its derivative, analogue and active fragment.

Base on the N terminal and C terminal amino acid sequence of the analgesic active peptide VGG (SEQ ID NO: 2), the corresponding oligonucleotide primers are designed respectively. In additionally, the oligonucleotide sequences corresponding to restriction sites for restriction enzyme NdeI and BamHI were added to the 5' terminal of above two primers (SEQ ID NO: 6 and SEQ ID NO: 7). The scorpion cDNA was used as the template for PCR amplification. The PCR products were analyzed by agarose gel electrophoresis, and the DNA product was cut from agarose gel for DNA extraction after the restriction enzyme NdeI and BamHI double digestion, which was ligated to a plasmid having been digested with NdeI and BamHI with T4 DNA ligase. The recombined plasmid was transformed into *Escherichia coli* competent cell DH 5α with common heat-shock protocol. The positive transformant was screened and selected. The plasmid was isolated from the bacteria. The isolated plasmid was verified with restriction enzymes and submitted to a biological technology service company for sequencing. The result indicates the analgesic active peptide VGG gene was successfully cloned into the plasmid from the above genetic engineering methods.

2. To Produce the Analgesic Active Peptide VGG and its Derivative, Analogue and Active Fragment.

The analgesic active peptide VGG gene was cloned in a plasmid and expressed in *Escherichia coli* for by using genetic recombination technique. The plasmid was isolated for sequencing. The plasmid was selected from pET-28a, pET-32a, pET-19b, pET-22b, pSYPU-1b and pSYPU-1c The plasmid contained a nucleic acid encoding a peptide having amino acid sequence as showed in SEQ ID NO: 3. The recombinant plasmid was transformed into *Escherichia coli* BL21 (λ DE3) by a heat shock protocol, then the single colony was isolated from LB solid media and inoculated to a tube with 3 ml LB liquid media (which contained 50 µg/ml of kanamycin), and the tube was put on a shaking incubator at 200 r/min for overnight culture at 37° C. By 1:100 ratio, the overnight culture was inoculated to a 400 ml triangle bottle with fresh LB media containing 50 µg/ml of kanamycin, and the bottle was put in a shaking incubator at 200 r/min for culture, shaking culture till OD600 is 0.6-0.8, the inducer IPTG was added at final concentration of 0.166 mmol/L inducer IPTG when the concentration of the culture was 0.6-0.8 of OD600, and cultures for additional 4 hours. At the end of culture, the bacteria were collected by centrifuged for 20 minutes at 3000 g in 4° C. The pellet was suspended with 40 ml of denaturing lysis buffer (0.1 M PBS, 0.15 M NaCl, 50 mM of imidazole) to suspended and ultrasonicated, which was centrifuged for 20 minutes at 12,000 g in 4° C. after the ultrasonication. The supernatant was saved. The precipitation was re-fragmented and treated as the same as above the pellet was treated. The two bulks of supernatant were combined and loaded on a metal ion chelating chromatographic column being balanced with 0.1 M PBS (pH 8.0). The column was washed with 5× volume of bed of column pH buffer for two times. Then, 0.5 M imidazole (pH 9.0) was used for elution, the eluent was yielded. Part of eluent was used for running a 15% SDS-PAGE to verify the purity of desired product. If the purity of the expressed product was not met the standard, the basic process of example 1 and 4 could be used until it meets standard.

The expressed product from above process was a peptide having amino acid sequence as showed in SEQ ID NO: 4. The separation and purification of the expressed product can be referred to the methods in examples 1 and 4.

According to the basic principle above, in between the peptide with amino acid sequence as showed in SEQ ID NO: 5 and the peptide with amino acid sequence as showed in SEQ ID NO: 2, has a hydrolysis site. The expressed product can be hydrolysis into the peptide with amino acid sequence as showed in SEQ ID NO: 5 and the peptide with amino acid sequence as showed in SEQ ID NO: 2 by using acid or hydroxyl amine, based on the properties of this hydrolysis site can be chemical hydrolysis at suitable conditions as an enzyme. The hydrolysis properties site can also be recognized by enterokinase, thrombase, coagulation X, etc. at specific hydrolysis conditions to digest the peptide bond. The expressed product were obtained through After the chemical hydrolysis or enzyme hydrolysis, the expressed product was converted into the peptide with amino acid sequence as showed in SEQ ID NO: 2. The separation and purification of the peptide with amino acid sequence as showed in SEQ ID NO: 2 were the same as the methods of example 1 and 4

3. The expression and purification of analgesic active peptide VGG in yeast. The analgesic active peptide VGG gene was amplified by using sequence using oligonucleotide primers, and a fragment of the gene was yielded. The 5' oligonucleotide primer (SEQ ID NO: 8) contained a restriction cleavage site of EcoRV restriction enzyme and an oligonucleotide whose sequence corresponding the N terminal of nucleic acid encoding analgesic active peptide VGG, the 3' primer (SEQ ID NO: 9) contained a restriction cleavage site of EcoRI restriction enzyme translational stop codon and an oligonucleotide whose sequence corresponding the C terminal of nucleic acid encoding analgesic active peptide VGG.

The site of restriction enzyme in primers can be ligated to the sites of restriction enzyme in yeast expression vector pPIC9K, (the enzyme incision of EcoRV and SnaBI are blunt ends), and this plasmid carries antibiotic resistance genes ($Amp^r$ and $Kan^r$), one replicon from the 2µ plasmid, another from AOX1 promoter, a high expression can be induced by methanol in *pichia pastoris*, a signal peptide sequence of α-factor, a termination signal, a HIS4 selected marker and integrated sequence.

The pPIC9K vector was digested with SnaBI and EcoRI, and the PCR product was digested with EcoRV and EcoRI, following by ligation. The ligated product was transformed into *E.coli* DH 5a bacterial with a common heat shock protocol, and the transformant was screened on LB petri dish which contained ampicillins. The selected clones were cultured in LB liquid media containing ampicillins for overnight. The plasmid was isolated and verified.

The linearized plasmid was electrically transformed into a yeast cell. A stable yeast transformant was produced by homologous recombination with homologous sequences of host genome. The high copy integrated transformants were screened by G418. The screened transformants were inoculated in 250 ml shake bottle which contained 25 ml MGY, BMG or BMGY medium, which was cultured at 28~30° C. 250~300 rpm for 16 to 18 hours. The concentration of culture was 2-6 of OD600. The yeasts were collected by centrifuge at 3000 g for 5 min at room temperature. The pellet was suspended at ⅕ to 1/10 of original culture volume in MM, BMM or BMMY (about 10~20 ml), which was in 100 ml shake flask, and sealed with double layer of gauze or rough cotton, and put it on a shaker (28~30° C./250~300 rpm) to culture, 100% methanol was added in the culture medium in 24-hour intervals until the final concentration of methanol was 0.5~1.0%. The supernatant was separated from above cultures, and loaded on ultrafiltration membrane, which retains molecular weight of 3000 Da, to remove the pigment. SDS-PAGE, Western-Blot analysis were used to detect the expression of the recombinant protein. The structural feature of the expressed product was a peptide with amino acid sequence as showed in SEQ ID NO: 2.

Example 6

1. In Vivo Analgesic Activity in Mouse Twisting Model Induced by Acetic Acid.

This example is used to test the in vivo biological activity of analgesic active peptide VGG, as well as its derivative, analogue and active fragment, with mouse twisting model induced by acetic acid.

The protein concentration was measured by using Lowry method.

In mouse twisting model: The glacial acetic acid as the chemical irritant is injected into the mouse stomach, which causes a deep and large area and lasting pain stimulus for animal which has a "twist body" reaction, such as abdominal cove, torso and legs spread out, hip high up.

Equal numbers of male and female mice, whose weight were about 18-2 g/each, were divided into groups by random. Each group consisted of eight mice. 0.2 ml/20 g of 0.6% (v/v) of acetic acid, which caused visceral pain, was intraperitoneally injected after the test sample was injected into the stomach of mouse for 20 minutes. The writhing times of the mouse were recorded for 10 min after the acetic acid was injected for 5 min. The morphine sample was use as positive control, normal saline as blank control. The inhibition of writhing response inhibition for each test group was calculated by the following formula:

$$\text{Inhibition Ratio} = \frac{\text{Writhing Times of Blank Group} - \text{Writhing Times of Medication Group}}{\text{Writhing Times of Blank Group}} \times 100\%$$

The results of analgesic biological activity shows:
(1) In the normal saline blank group, the writhing times (Mean±SEM) was 45.32±2.57. In positive control group (morphine, 3.51 μmol/kg), the writhing times (Mean±SEM) was 29.12±1.76, the inhibition of writing was 35.75%.
(2) The various purity of analgesic active peptide VGG, which were isolated from scorpion venom or scorpion tails or scorpion body, groups, the inhibition of the animal writhing was 50% and above when the test sample dosage was 0.1 mg/kg-1.0 mg/kg (test sample/mouse weight).
(3) In the purest analgesic active peptide VGG group, the inhibition of the animal writhing was 60% and above when the test sample dosage was 0.1 mg/kg (test sample/mouse weight).
(4) In the analgesic active peptide VGG and its derivative, analogue and active fragment test samples, which were isolated from recombinant bacteria or yeasts, groups, the inhibition of the animal writhing was 50% and above when the test sample dosage was 0.1 mg/kg (test sample/mouse weight).

2. In Vivo Assay of Analgesic Activity—Hot Plate Method of Mice

This example is used to verify the in vivo biological activity for the analgesic activity of analgesic active peptide VGG with mouse twisting model.

The mouse hot plate analgesic method: the female mice with weight from 18 g to 22 g were put a hot plate at temperature of 55±0.5° C. which was maintained by a water bath. The licking times were recorded plate as the pain threshold of mouse after it was put onto the hot plate. The pain threshold between 10-30 seconds was considered to be qualified for experiments. The qualified mice were divided into groups by random. The normal pain reaction time of mouse was determined for two times. The mean of the pain threshold (B) was calculated before medicine was taken. The analgesic active peptide VGG (dosage of 0.1 mg/kg (test sample/mouse weight) was intravenously injected via tail. The normal saline was used as control group. The pain reaction time was recorded as one at 15, 30, 45, 60 seconds after the test sample was taken. The mouse was immediately taken out if it had no pain response on the hot plate in 60 seconds. The 60 seconds as a calculation unit, the pain threshold increasing percentage was calculated by the following formula:

$$A = (B-C)/C \times 100\%$$

A—Pain threshold increasing percentage
B—Average response time after medicine taken
C—Average response time before medicine taken The results of analgesic biological activity experiment were shown in the table:

| Time | Analgesic Active Peptide VGG | | NS | |
|---|---|---|---|---|
| | B (s) | A (%) | B (s) | A (%) |
| Before | 21 ± 4.2 | — | 30 ± 5.1 | — |
| 10 min | 48 ± 3.2 | 128 | 44 ± 5.4 | 42 |
| 15 min | 50 ± 5.1 | 138 | 47 ± 6.3 | 52 |
| 30 min | 45 ± 3.7 | 114 | 38 ± 3.4 | 23 |
| 45 min | 42 ± 6.9 | 100 | 43 ± 6.6 | 39 |
| 60 min | 40 ± 3.5 | 90 | 40 ± 4.7 | 29 |

What is claimed is:

1. A process for purifying an analgesic peptide, wherein said analgesic peptide is SEQ ID NO: 2, comprises the following steps:
   (1) dissolving a scorpion in distilled water or acid solution or alkaline solution, and removing the insoluble impurities by a centrifuge, and taking the supernatant as a leaching liquid for further purification, wherein the pH is between 2 and 12, the temperature is between 0 and 45° C.;
   (2) using a hydrophobic chromatography column to separate an analgesic active component I from the leaching liquid, wherein the pH is between 5 and 9, the concentration of neutral salt in elute is between 0.5 to 2 M, the neutral salt is selected for the group consisting of $(NH_4)_2SO_4$ or $Na_2SO_4$ and NaCl;
   (3) removing salt and non-essential proteins from said analgesic active component I by ultrafiltration, and obtaining an analgesic active component II with concentration by an ion exchange chromatographic column, wherein a ultrafiltration membrane is selected from the group consisting of the membranes permeating 10-50 kDa of peptides and the membranes retaining 1-5 kDa of peptides;
   (4) obtaining an analgesic active component III from the analgesic active component II by a hydrophobic chromatographic column;
   (5) obtaining an analgesic active component IV from the analgesic active component III by an ion exchange chromatographic column, wherein the pH is between 2 and 12, the concentration of salt in elute is between 0.1 to 0.5 M, the salt is selected for the group consisting of $(NH_4)_2SO_4$ or $Na_2SO_4$, NaCl, and KCl;
   (6) obtaining the scorpion analgesic peptide VGG from the analgesic active component IV with a gel filtration chromatography, wherein the gel filtration chromatography is selected from the group consisting of Sephacryl S-100 HR or Sephacryl S-200 HR or Sephadex G-50 or Sephadex G-75 or Sephadex G-100 or Sephadex G-150 or Superose 12 prep grade or Superose 6 prep grade or Superdex 30 prep grade or Superdex 75 prep grade or Superose 12 HR or Superose 6 HR or Superdex Peptide HR or Superdex75 HR and Superdex Peptide PE, the ion concentration of eluent is 0.15-1M;

(7) further purifying the analgesic active peptide VGG by a reversed phase chromatographic column, wherein the organic solvent of the eluent is selected from the group consisting of acetonitrile, methanol and tetrahydrofuran, the concentration of organic solvent in the eluent is 20%-90%.

* * * * *